United States Patent [19]
Costello et al.

[11] Patent Number: 5,289,253
[45] Date of Patent: Feb. 22, 1994

[54] PATTERN SCANNING DEVICE

[75] Inventors: Brendan D. Costello, Meadow House, Sibton Road, Peasenhall, Suffolk; David R. Winterbottom, Colchester, both of England

[73] Assignee: Brendan D. Costello, Suffolk, England

[21] Appl. No.: 761,982

[22] PCT Filed: Mar. 23, 1990

[86] PCT No.: PCT/GB90/00450
§ 371 Date: Nov. 12, 1991
§ 102(e) Date: Nov. 12, 1991

[87] PCT Pub. No.: WO90/11047
PCT Pub. Date: Oct. 4, 1990

[30] Foreign Application Priority Data
Mar. 23, 1989 [GB] United Kingdom ............... 8906816

[51] Int. Cl.⁵ ............................................. G06K 9/20
[52] U.S. Cl. .................................................. 356/71
[58] Field of Search ................... 356/71; 382/4, 5

[56] References Cited
U.S. PATENT DOCUMENTS

| | | | |
|---|---|---|---|
| 3,826,562 | 7/1974 | Baumgardner et al. | 359/831 |
| 3,864,042 | 2/1975 | Leventhal | 356/71 |
| 4,385,831 | 5/1983 | Ruell | 356/71 |
| 4,537,484 | 8/1985 | Fowler et al. | 356/71 |
| 4,783,167 | 11/1988 | Schiller et al. | 356/71 |
| 4,925,300 | 5/1990 | Rachlin | 356/71 |

Primary Examiner—Richard A. Rosenberger
Attorney, Agent, or Firm—Charles D. Gunter, Jr.

[57] ABSTRACT

The present invention relates to a device for scanning the surface of a generally cylindrical object carrying a raised pattern, such as a finger, which device comprises:
a. a transparent optical body having a substantially arcuate configuration about a first axis and having an axial cross-section which is convergent for at least part of its radial dimension, and a channel parallel to and substantially co-axial with that axis, which channel presents a face substantially parallel to the said axis, upon which the object whose surface is to be observed can be placed;
b. a source of incident light adapted to be directed onto a light entry face of the convergent cross-section of the body, the configuration of the body being such that the incident light is adapted to strike the under-side of the said base face at substantially the angle of total internal reflection and to be reflected through the same or another face of the convergent cross-section of the body;
c. means for causing the incident light from said source to illuminate the surface of an object placed in contact with the planar face of the channel; and
d. a means for observing the light reflected from the underside of the base face through a face of the convergent cross-section of the body and for providing a signal dependent upon the intensity of the light detected.

16 Claims, 6 Drawing Sheets

PATTERN SCANNING DEVICE

The present invention relates to a device, notably to a device for capturing the image of any friction skin surface area of a human or other animal, for example the finger print of a person.

BACKGROUND TO THE INVENTION

The skin on the finger of a person carries raised friction ridges on it which follow a distinctive pattern which is unique to that person. Other areas of the skin of the body of a human or other mammal, for example a horse, also carry such raised friction ridges, e.g. the palm of the hand, or the toes or heel of the foot. For convenience the term finger print will be used herein to denote generally any friction skin surface area on the skin, and specifically that raised friction ridge pattern on the final segment or tip of a human finger.

The ridge pattern of a finger print can be visually scanned and analyzed by a skilled observer in order to establish whether the finger print corresponds to one left at the scene of a crime, or to one which is submitted to establish the identity of the person. This requires a highly skilled observer and can be cumbersome and it would be desirable for that operation to be carried out using some form of electronic pattern recognition system.

It has been proposed to scan a finger print using a light source so as to plot the position and type of the characteristics contained within the ridge patterns on the fingerprint. In one type of system, the finger is placed upon one face of a transparent material, for example a sheet of glass, and light is shone onto the opposite face of the material so that the light strikes the underside of the first face at substantially the angle of total internal reflection. Where the ridges of the finger print contact the surface of the material, they alter the angle of total internal reflection and part of the incident light passes through that face of the material and part is reflected back as scattered light. By way of contrast, the incident light is totally internally reflected at those areas where the skin does not contact the material, i.e. those areas where the valleys in the finger print pattern are located.

By illuminating and scanning individual points across the surface of the material, it is possible to build up a picture of light and dark points so as to form an image of the finger print. When viewed along the line corresponding to the exit direction for the totally internally reflected light, a dark image is perceived at the point of contact and a light image where there is no contact, giving a positive image. When viewed from a position significantly offset from the exit path of the totally internally reflected light, the scattered light from the regions where the ridges contact the surface is perceived, but no light is detected from the regions where there is no contact, so that a negative image is perceived.

The image can be scanned electronically to detect the light and dark areas and to convert those into electrical signals which can be recorded as an electronic image of the fingerprint pattern. Either the positive or the weaker negative image can be used to detect the pattern of the ridge lines and features thereon. For convenience, the invention will be described hereinafter in terms of scanning the positive image.

Typical of such systems is that described in U.S. Pat. No. 4,537,484 where the finger is placed upon a channel of transparent material and the light and dark images are scanned to give an electronic record of the image. This is achieved by mounting an elongated light source on a rotating carriage so that an axial strip of the finger print pattern is illuminated and scanned through the under surface of the channel. The carriage also carries a mirror and lens system by which the light reflected from the under surface of the channel can be directed onto an array of light sensitive diodes, arranged axially along the axis of rotation of the carriage, so to generate electronic signals corresponding to the light and dark areas of the image being scanned. The carriage is rotated by a stepper motor to illuminate and scan a series of axial strips of the under surface of the channel so as progressively to build up a total scan of the under surface of the channel. The images perceived by the diode array are read out into a suitable image processor and verified against a record of that persons finger print.

Such a mechanism is complex and expensive to construct and requires the use of high optical quality lenses to focus an elongated image accurately onto the diode array. A further problem is that there may be reflections from the various faces of the channel as well as from the under surface of the face in contact with the finger print. At least part of those other reflections may be internally reflected within the wall of the channel and combine with the totally internally reflected incident light from the desired part of the channel to give a scattered light for scanning by the diode array. This could lead to a loss of definition in the perceived image resulting in rejection of images as unclear. Also, some of the incident light is dissipated by these other reflections reducing the intensity of the light perceived by the diode array.

I have now devised an optical body and scanning device using that body which is reduces the above problems.

SUMMARY OF THE INVENTION

Accordingly, the present invention provides a device for scanning the surface of a generally cylindrical object carrying a raised pattern thereon so as to detect that pattern, characterized in that the device comprises:

a. a transparent optical body having a substantially arcuate configuration radially about a first axis and having an axial cross-section which is convergent for at least part of its radial dimension, and a channel parallel to and substantially co-axial with that axis, which channel presents a face substantially parallel to the said axis, upon which the object whose surface is to be observed can be placed, and the underside of which face serves as the optical base face to the body;

b. a source of incident light adapted to be directed onto a light entry face of the convergent cross-section of the body, the configuration of the body being such that the incident light is adapted to strike the under-side of the said base face at substantially the angle of total internal reflection for the material from which the body is fabricated and to be reflected through a face of the convergent cross-section of the body;

c. means for causing the incident light from said source to illuminate the surface of an object placed in contact with the face of the channel; and d. a means for observing the light reflected from the underside of the base face through a face of the convergent cross-section of the body and for providing a signal dependent upon the intensity of the light detected.

Preferably, the means for observing the light from the face of the body progresses axially and transversely across the said base face; and the light reflected from the underside of the base face is observed through the third face of the convergent cross section of the body.

The transparent optical body is novel and the invention therefore also provides a transparent optical body having:

a. a substantially arcuate configuration about a first axis;

b. a portion having an axial cross-section which is convergent for at least part of its radial dimension; and c. a channel substantially parallel to and co-axial with the said axis, which channel presents an exposed face substantially parallel to the said axis, the underside of which serves as the optical base face to the convergent cross section to the body;

the configuration of the body being such that an incident light beam shone onto one face of the convergent cross-section of the body is adapted to strike the underside of the said base face at substantially the angle of total internal reflection for the material from which the body is fabricated and to be reflected through the same or another of the faces of the convergent cross-section of the body.

Preferably one of the incident or reflected light paths is substantially normal to the plane of the face of the body through which it passes.

Figure 1:
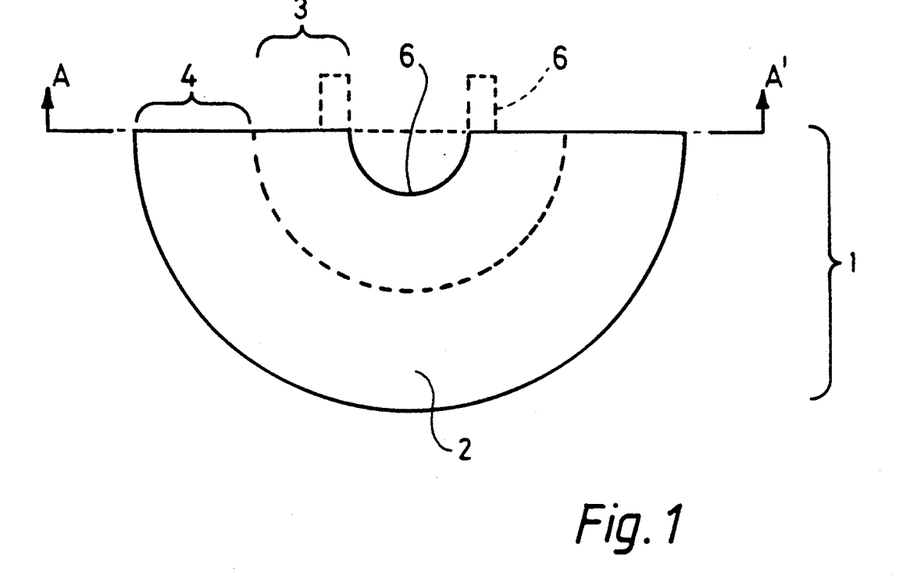
FIG. 1 is a radial cross-section through a transparent optical body of the invention.

The term radial cross-section is used herein in respect of the body to denote a cross section through the body in a plane transverse to the longitudinal axis of the body and extending radially from that axis, that is the cross-section shown in FIG. 1 of the accompanying drawings.

Figure 2:
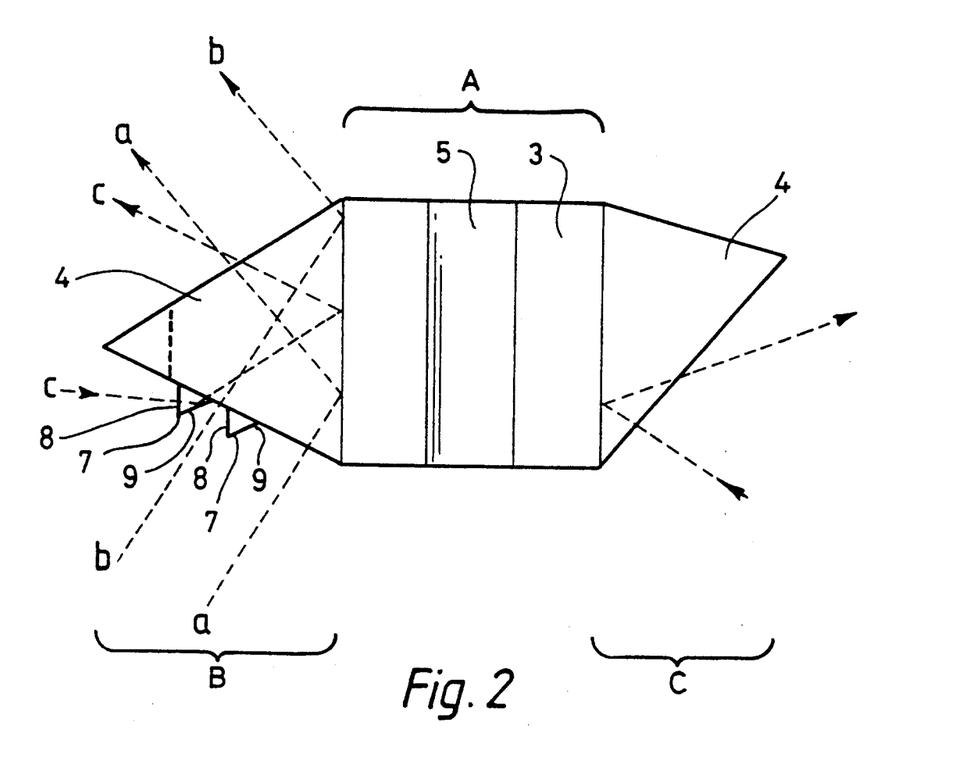
FIG. 2 is an axial cross-section through the body of FIG. 1 along the line A-A' and showing two alternative cross-sections B and C.

The term axial cross section is used herein to denote a cross-section through the body in a plane parallel to the longitudinal axis of the body and extending radially from that axis, that is the cross-section shown in FIG. 2 of the accompanying drawings.

The term transparent as used herein denotes a material through which light can be transmitted and which does not significantly scatter a light beam passing through the material.

The invention further provides a method for scanning a raised pattern on the surface of an article by scanning the totally internally reflected light from that surface using an optical body of the invention.

DESCRIPTION OF THE DRAWINGS

To aid understanding of the invention, it will hereinafter be described in terms of a preferred form thereof as shown in the accompanying drawings in which.

DESCRIPTION OF THE PREFERRED EMBODIMENT

The optical body 1 of the invention comprises a generally arcuate member 2. The member 2 can extend over a full 360° arc, but preferably extends over 120° to 240°, notably over about 180°. The member 2 is preferably substantially symmetrical about its longitudinal axis, but the extremes of the arc can be formed with a different cross-section and shape to provide mounting means for the member 2 if desired and if scanning through those extremes is not required.

The body has a convergent axial cross-section. The convergence can extend uniformly from the longitudinal axis of the body so that the whole of member 2 has a triangular axial cross-section; or the body can have a radially inward non-convergent section carrying a radially outward convergent section. For example, as shown in the cross-section of FIG. 2, the body can have a generally cylindrical central portion 3 adjacent its longitudinal axis having a rectangular radial cross-section A shown in FIG. 2, with a triangular cross-section portion 4 extending radially outward from the cylindrical portion.

The convergent cross-section portion of the body preferably has a generally triangular axial cross-section, but this need not be a symmetrical triangle. Thus, the triangular cross-section portion 4 can be radially symmetrical as shown in the left hand portion B of cross-section of FIG. 2, or can be an irregular triangle, as when one face of the triangle is inclined to a greater angle to the axis of the body than the other, as shown in the left hand portion C of the cross-section of FIG. 2. The triangular cross-section can be truncated as shown dotted in portion B of FIG. 2, for example, to give a quadrilateral cross-section having two opposed sides converging and the other two opposed sides parallel or divergent, since it has been found that such a shape reduces reflection of incident light from one face onto the other faces of the body. The body thus acts in the manner of a prism to reflect internally from one internal face of the body light which is shone into the body through another face.

The body is formed with an axial channel 5 in or on member 2 located substantially parallel to the axis of the body. It is preferred that the channel be formed substantially co-incident with the axis of member 2 so that the body is radially and axially symmetrical and provides an arcuate surface 6 upon which the object to be scanned rests. The channel 5 is preferably a simple circular radial cross section channel extending the full axial length of member 2. However, if desired, the channel can have an end wall, for example in the form of a hemispherical surface, to provide an axial stop against which the object to be scanned butts so as to locate it at a predetermined position with respect to the body 1. Where the member 2 extends through a 360° arc, it will be appreciated that the channel may be in the form of a bore through the member 2, or an axially extending slot may be formed in the member 2 to permit radial as opposed to axial entry into the channel 5. For convenience, the invention will be described hereinafter in terms of an open topped channel 5 into which the object to be scanned is placed through the open top of the channel.

The bottom wall of the channel 5 provides a face upon which the object to be observed is placed. This face may be a flat face, as when the channel walls 6 are formed upstanding from a diametric transverse face of the member 2, as shown dotted in FIG. 1. However, it is particularly preferred that the channel be formed within member 2 with its axis substantially co-incident with the axis of the member, since this will simplify the optical path of the incident and exit light and reduce the need to compensate for different geometries where a flat faced channel is used. The wall 6 thus presents a curved profile in radial cross-section of the channel and a substantially linear face in axial cross-section of the channel.

The channel 5 is to receive and locate the object to be scanned.

The object is preferably the end portion or tip a finger of a person, but the invention can be applied to the detection of raised patterns on other objects, for example to scan the surface of a metal tube or rod for surface imperfections. For convenience, the invention will be described hereinafter in terms of the scanning of a human finger tip, and the channel 5 and member 2 will be dimensioned accordingly.

As stated above, the under-side of the wall 6 of channel 5 serves as the optical base for the convergent cross-section portion of the member 2. It is therefore preferred that this face be a smooth as practicable, for example by being polished using conventional techniques. If desired, the wall of the channel can be given a surface coating to improve its optical properties and/or to modify the angle of total internal reflection where desired, for example where for structural reasons it is not possible to use a material having an angle of total internal reflection which enables to member 2 to have the desired dimensions or shape.

As stated above, the perceived intensity of the reflection of an incident light beam falling on any one point on the under-side of the wall 6 of the channel will depend upon whether a ridge contacts the channel wall at that point or not. In order to simplify the illumination and scanning of each selected point on the under-side of the channel wall, it is preferred that the light path through the member 2 follow a substantially consistent pattern where the source of the illumination is moved axially and circumferentially with respect to member 2. To this end, it will usually be preferred that the incident light fall at a substantially constant angle on a light entry face into the member 2, that it strikes the under-side of the wall of the channel at substantially the angle of total internal reflection and that the reflected light exits through the same or another face of member 2 at an angle substantially normal to the plane of that face. As a general guide, it is preferred that the incident light fall at an angle which is ±5° to normal to the plane of the entry face, that it strikes the under-side of the wall 6 of the channel at ±0° to the angle of total internal reflection and that the reflected light exits at ±5° to normal to the plane of the exit face.

The optimum angles for the convergent cross-section and the overall dimensions and configuration of member 2 and the channel 5 can readily be determined by theoretical consideration of the light paths and the material from which member 2 is made using conventional optical theory and calculations. The light path can be selected so as to suit the dimensions of the device in which the member 2 is to be used. Thus, with the form of cross section for portion C shown in FIG. 2, it may be possible to direct the light reflected from the under-side of the channel wall onto a detecting sensor through the same face of the triangle as that through which it enters. However, with the cross-section of portion B shown in FIG. 2, the reflected light beam will usually exit through the opposite face of the triangle of the convergent section to that through which it enters.

Preferably, the body is made from glass or a substantially clear machinable or castable plastic having an angle of total internal reflection which enables the desired light paths to be achieved. The total internal reflection angles quoted herein are for the interface between the material and air, since the member 2 will usually be used in ambient conditions. Examples of suitable optical grade polymeric materials from which member 2 can be made include polyvinylic resins, polystyrene resins, polyacrylic or polymethacrylic resins, polycarbonate resins or polyester resins. If desired, alloys or co-polymers containing these resins may be used to achieve the desired optical properties. A particularly preferred resin for present use is a polymethylmethacrylate resin, notably that commercially available under the Registered Trade Mark Perspex. With such a material, the cross section for portion C shown in FIG. 2 will typically have included angles of from 60° to 90° at the apex and from 45° to 60° at each base angle.

Figure 4:
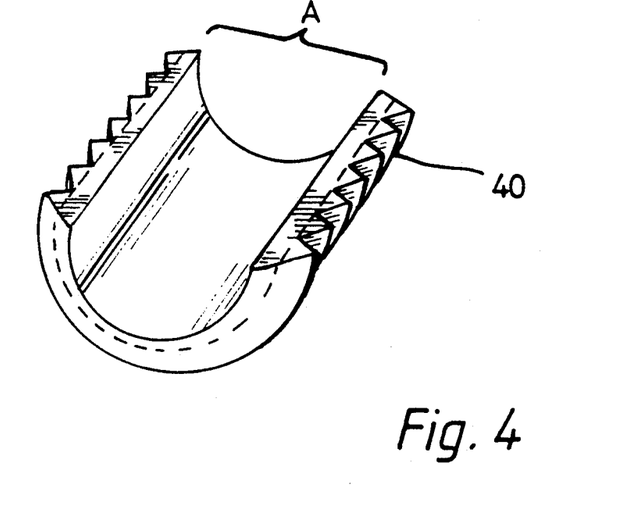
FIGS. 4 and 5 show alternative forms of the optical body for use in the scanning system of FIG. 3.
Figure 5:
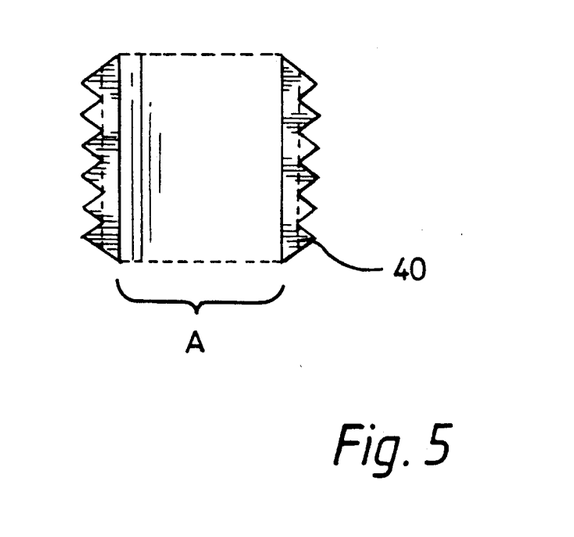

The member 2 will usually be of unitary construction. However, it is within the scope of the present invention for member 2 to be formed in two or more parts made from different materials. Thus, the cylindrical central portion 3 could be formed from one material and an annular triangular cross-section portion B then secured upon that section to give a composite construction where it is desired to modify the light paths within the member 2. Alternatively, the body may be made from a plurality of thin disc-like members 2 to form an elongated body having a series of arcuate triangular ridges thereon, as shown in FIGS. 4 and 5. For example, as shown in FIGS. 4 and 5, such a body can comprise the cylindrical portion A of the body of FIG. 2 with a series of adjacent arcuate triangular portions 40 extending radially from the outer surface of the cylindrical portion. The surface of such a body thus presents a saw tooth type of outer surface to the incident light and each saw tooth behaves in a manner similar to the single body described above.

If desired, the geometry and materials of construction of the members 2 used in such a composite structure can be varied from member to member to vary the optical properties of the body along its axial length. If desired, each opposed radial face of the cylindrical portions of members 2, notably in such a composite structure, can carry a silvered or other optical barrier to reduce the transmission of light from one member 2 to another.

Member 2 can be formed in any suitable manner, for example by casting or machining the desired shape from a suitable material. The faces of the member will usually be polished to provide substantially perfect optical plane surfaces using conventional optical manufacturing techniques. However, it may be desired to form either or both of the entry and exit faces with circumferential arcuate grooves or the like in the surface thereof whereby the faces incorporate lens or reflective features for focusing light upon specific portions of the under-side of the wall 6 of the channel and/or to refract a light beam entering the member to enable the light paths to follow a desired direction. Thus, as shown in FIG. 2, the entry face can be provided with a series of saw tooth circumferential ridges 7 which provide a series of parallel entry faces 8 and reflective faces 9 at varying angles to the longitudinal axis of member 2 whereby incident light from a radial direction falls at a consistent angle upon the under-side of the wall 6 of the channel.

The surfaces of member 2 can be given coatings or surface treatments to enhance their optical performance using conventional optical techniques.

The optical body described above finds use in the scanning of finger print patterns on a finger placed in channel 5. As stated above, the ridges on the finger cause variations in the angle of total internal reflection at the point of contact with the channel wall 6 which can be detected by one or more conventional optical sensors scanning the reflected light leaving member 2. Where a substantially uniform illumination can be achieved across the whole of the face of member 2 through which the light is to enter, it may be possible to use a stationary light source adjacent that face, for example an array of light emitting diodes or point source illuminations, to illuminate each point both axially and circumferentially on the under-side of the wall 6 of the channel to be scanned. The light reflected from the under-side of the wall can be detected by stationary sensors set to correspond with each point on the wall to be scanned so that the light intensity is scanned electronically.

However, this may be difficult and expensive to achieve with current technology and it is preferred to illuminate the under-side of wall 6 with a point light source which traverses the surface of the wall axially and circumferentially so as to illuminate all points on the under-side of the wall to be scanned.

Thus, a point source, for example a laser or a collimated and/or focused light beam, can be moved circumferentially and radially across the entry face of the convergent cross-section of member 2 by means of a suitable mechanism. As shown by the dotted light beams a and b in FIG. 2, this will cause the light beam to traverse the under-side of the wall of the channel both axially and circumferentially. Typically, such a mechanism will comprise a series of mirrors, at least some of which are carried by a rotating member so as to achieve the circumferential movement of the light upon the entry face; and the rotating member is moved axially to achieve the desired radial movement over the entry face.

The rotational and axial movement of the mechanism are interlinked so that the entry face is illuminated in an orderly sequence. Thus, the rotational member can be moved axially by means of a stepper motor, one step for each complete rotation of the rotational member. If desired, where member 2 extends over less than 360°, the rotational member can rotate in alternate directions rather than continuously in the same direction.

The light reflected from the under-side of wall 6 of the channel can be detected by any of a wide range of sensors, preferably ones which emit an electrical signal in response to the intensity of the light falling upon them. As with the illumination, the sensors can be arranged as a static array of sensors, for example light sensitive diodes or charge couple devices, set to receive a beam of light from each point on the under-side of the channel wall 6 to be scanned. However, this may be complex, and we prefer to cause a single sensor to receive the light from the exit face of member 2. This can be achieved by mounting the light sensor on the same rotating mechanism as the light source so that it moves in synchrony with the light source to scan the exit face of member 2.

However, we have found that this can lead to problems due to the transmission of vibration from the rotating mechanism to the light source and/or sensor and problems may arise in the generation of electrical interference when signals are transmitted through slip rings or the like from the sensor to a static image processing circuit. We therefore prefer that the light source and the light sensor be mounted separate from the rotating mechanism.

Figure 3:
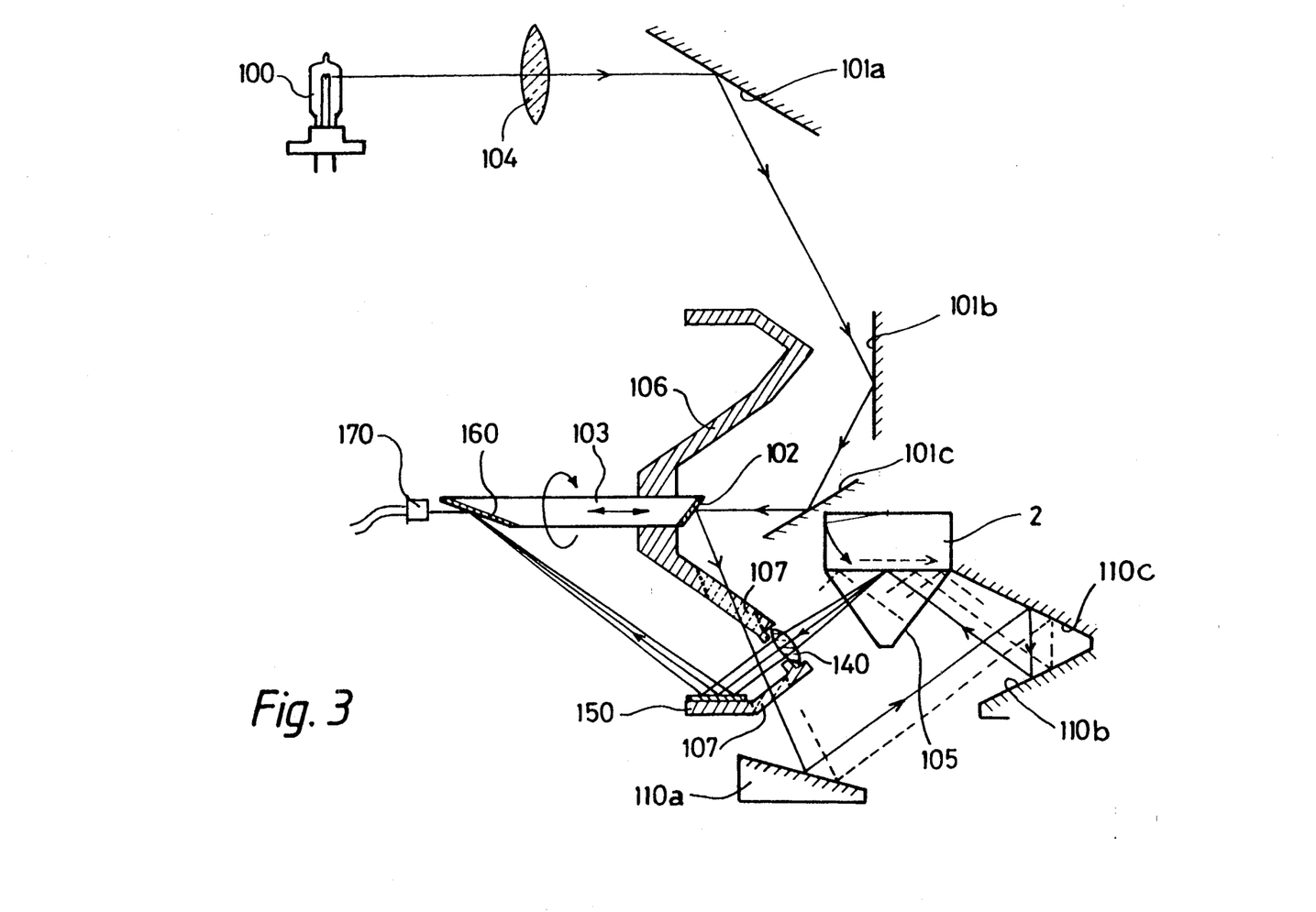
FIG. 3 is a diagrammatic cross-section through an optical system for scanning the friction ridge pattern of a finger placed in the channel member of a scanning device incorporating the optical body of FIG. 1.

A particularly preferred form of such a device incorporating a stationary light source and a non-rotating light sensor is shown diagrammatically in FIG. 3. The device comprises a light source 100, for example a collimated light source or a laser, which projects a beam of light onto a series of static mirrors 101a, b and c so that the light beam is directed axially onto a mirror or polished end face 102 on a rotating shaft 103. Where a lamp light source is used, the beam from that source can be focused using a conventional lens system 104 onto the first mirror 101a of the series. By using a mirrored face 102 on the axis of rotation of the shaft 103, the line of direction of the light beam thereafter is caused to rotate with the shaft and so to follow a circumferential traverse of the entry face 105 of the member 2 as described above. Also, the direction of the light beam will be substantially unaffected by reciprocation of the rotating parts of the device as described below.

A rotating member 106 is carried on shaft 103. This member supports one or more further mirrors for directing the beam of light from the mirror system 101 and the mirrored face 102 of shaft 103 onto the entry face 105 of member 2. In some cases, the rotating member 106 does not carry further mirrors, but the light beam is passed through one or more apertures 107 in the member to a further system of static mirrors 110a, b and c which direct the light from the end of shaft 103 onto the entry face 105 of member 2 as shown. Since the member 106 is rotating, the mirror 102 imparts a circular path of travel to the light beam so that it sweeps out a conical surface of revolution. The mirrors 110a, b and c are formed as arcuate mirrors extending over the required arc of that cone of revolution to ensure that the beam from face 102 is reflected onto the entry face 105 of member 2 over the desired arc.

The light entering member 2 strikes the under-side of the channel wall 120 and is reflected as shown to exit from member 2 through the exit face 130. Since the reflected light beam is rotating in synchrony with member 106, the reflected light beam can be re-directed by one or more mirrors carried by member 106 to strike a light sensor monitoring the intensity of the reflected light beam. There will usually be some scattering of the reflected light, and it is preferred that the reflected light beam be focused by a lens system 140 onto a mirror 150, both carried by the rotating member 106.

The light beam from mirror 150 preferably directs the light beam from lens 140 onto a further mirror or polished end face 160 on the shaft 103, which directs the light beam axially onto a light sensor 170 located on a mount aligned with the axis of rotation of the shaft 103. By re-directing the reflected light beam onto components carried by the rotating member 106 and thence onto the mirrored end 160 of shaft 103 forming the axis of the rotating member 106, the rotating sweep of the light beam introduced by the initial mirror system is counteracted so that the light beam from the mirrored end 160 of the shaft can be directed axially onto a non-rotating light sensor thus avoiding the need for rotation of the sensor.

The light sensor 170 can be selected from a wide range of types, but is preferably one which emits an electrical signal whose value is related to the intensity of illumination falling upon it, for example a photosensitive diode or the like.

As member 106 rotates about its axis, which is substantially parallel to the axis of member 2, it causes the light beam from source 100 to sweep an arcuate path across the entry face 105 of member 2. This causes an arc of the wall 120 of the channel 5 to be illuminated. In order that the required axial area of the wall be scanned, it is necessary to cause member 106 to reciprocate axially. As described above, this causes the light beam from the rotating member to sweep the wall 6 axially.

Alternatively, one or more of the mirrors 110 can be tilted to re-direct the beam of light from the end 102 of the shaft, but this may be complex.

The axial reciprocation of the rotating member can be achieved by a number of ways. Thus, the shaft 103 carrying the rotating member 106, together with the sensor 170 can be mounted on a carriage 180 which is moved axially by a screw drive, rack and pinion drive or other means by the drive from the motor rotating member 106. However, it is preferred to drive the carriage 180 by means of a stepper motor which moves the carriage in increments at each rotation of member 106. Member 106 can carry indexing means, for example a slot or tab whose passage is sensed by a photoelectric sensor, Hall effect sensor or other proximity switch to operate the stepper motor. The carriage 180 is preferably supported on guide rails, rods or the like so that it moves axially along the desired path.

Figure 6:
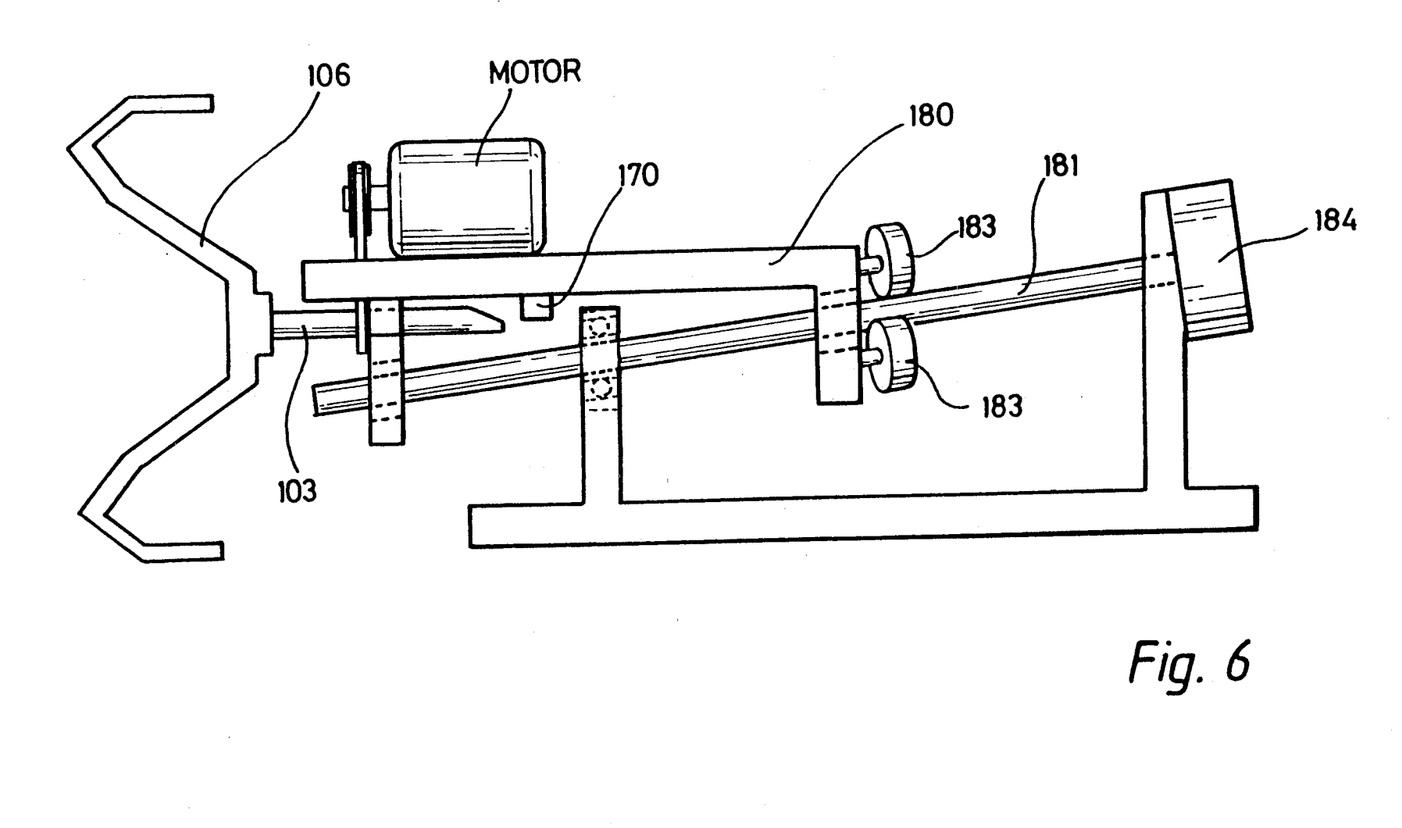
FIG. 6 shows in diagrammatic form means for axially moving the rotating mechanism of the device of FIG. 3.

In order to compensate for slight differences in light path lengths where an optical body 2 as described above is used, it may be necessary for member 106 to move vertically as well as axially, whilst keeping its axis of rotation substantially parallel to the axis of the body 2. This can be achieved by reciprocating member 106 along a line at an angle, usually in the range 5° to 15°, to the true axis of rotation of member 106. The optimum angle can readily be determined from a study of the geometry of the system and the combined axial and vertical movement can readily be achieved by reciprocating the carriage 180 described above along a support, for example a ramp or support shaft, which is at the required angle to the axis of rotation of member 106 as shown in FIG. 6.

In a particularly preferred embodiment for reciprocating the carriage 180, the carriage 180 is mounted by suitable sliding bearings for axial movement upon two or more support shafts 181 carried by the base or main frame of the device. The shafts 181 are inclined at from 5° to 15° to the horizontal so that the carriage 180 moves vertically as it moves axially upon the shafts, the orientation of the axis of rotation of member 106 remaining substantially unaltered. The carriage 180 carries one or more ball races 183 each rotating about a stub axle which is mounted at an angle to the axis of one of the shafts 181 and bearing against the shaft 181. A stepper motor 184 rotates shaft 181. Due to the inclination or skew of the ball races, the rotation of the shaft 181 causes the ball races to move axially with respect to the shaft 181. The greater the skew of the races, the greater the axial movement per rotation of shaft 181. It is preferred to use three such skewed ball races bearing against the one shaft 181 and that they be skewed at angles of from 1° to 30° to the axis of rotation of shaft 181. Such a drive system is simple and effective and maintains the correct orientation of the axis of rotation of member 106 with respect to the body 2 whilst compensating for the change in optical paths by achieving the desired vertical movement of member 106 with respect to body 2.

The above system is one example of a system by which the light from a stationary source can be caused to traverse axially and circumferentially over the underside of the wall 6 of the channel 5 in the optical body and be returned to a non-rotating light sensor. It will be appreciated that the device can be modified in a number of ways whilst still retaining the concept of rotating and then counter-rotating a light beam. Thus, the mirror arrangement can be such that the light source 100 is located below the optical member 2 so that the height of the device is reduced; or the configuration of member 2 and the mirrors is such that the beam of light enters and leaves member 2 through the same face.

Figure 7:
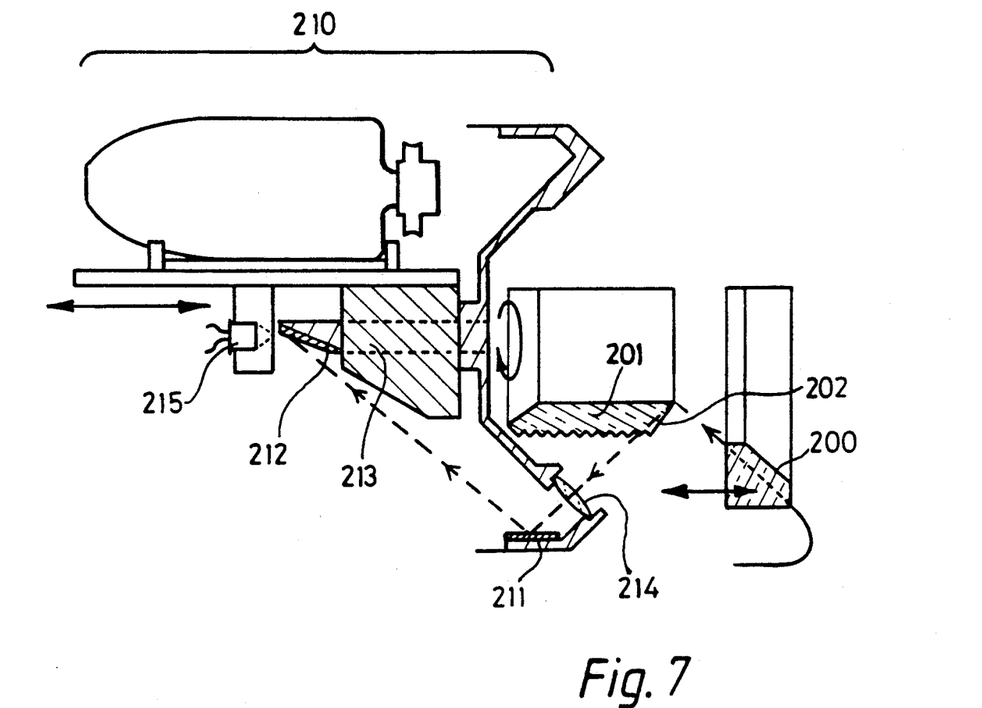
FIG. 7 is a diagrammatic side view of an alternative to the scanning system of FIG. 3.
Figure 8:
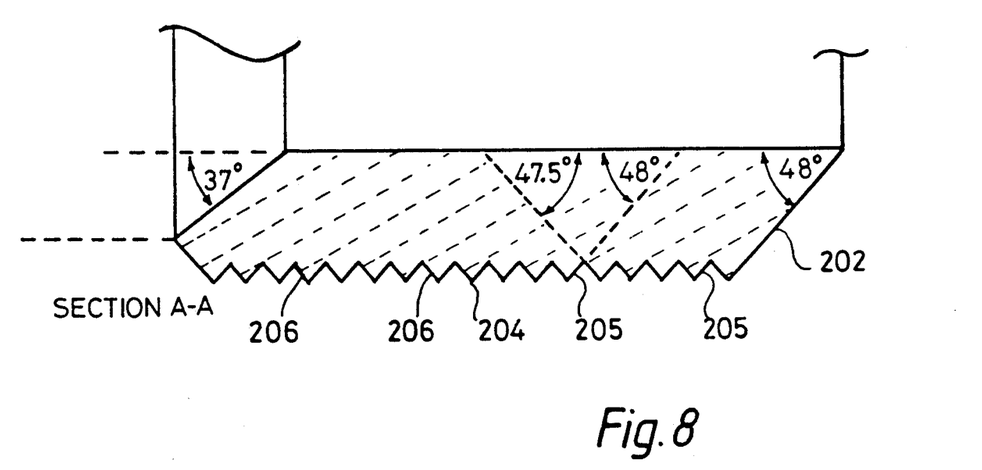
FIGS. 8, 9 and 10 are axial cross-sectional, radial cross-sectional and perspective views of the optical body for use in the system of FIG. 7.
Figure 9:
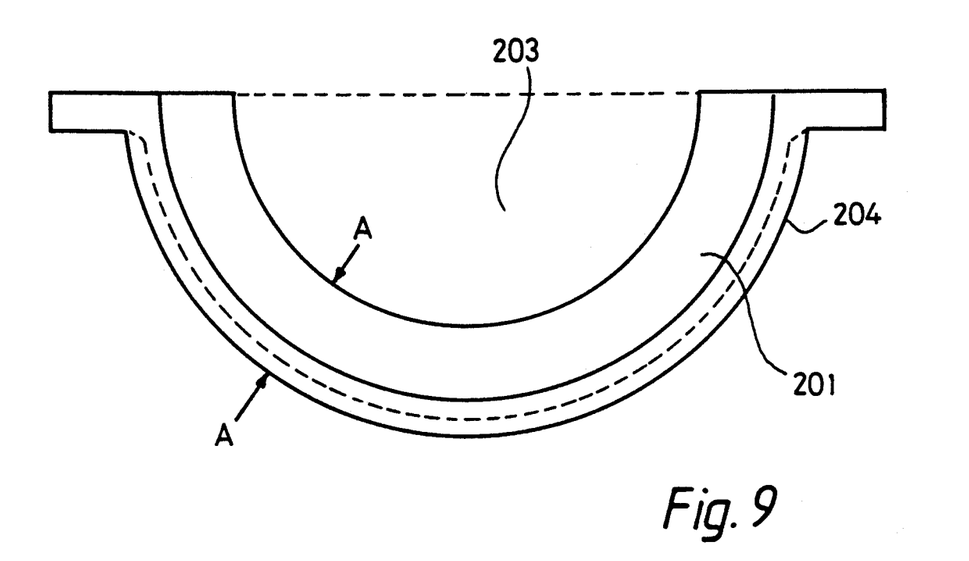
Figure 10:
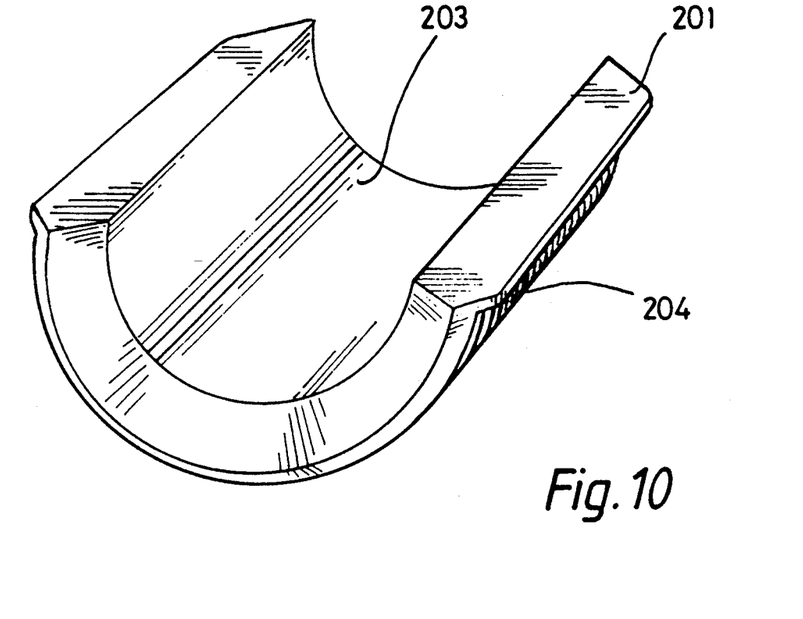

In the alternative form of device shown in FIGS. 7, 8, 9 and 10, an arcuate array of optical fibers 200 or other point sources of illumination is arranged to direct an arc of light onto an arcuate optical body 201 through an entry face 202. The longitudinal axes of the array and the optical body are substantially co-incident. As shown in FIGS. 7, 8 and 9, the body comprises a generally semi-cylindrical portion having a semi-circular radial cross-section, made from a suitable optical grade machine-able or castable resin, for example a polymethylmethacrylate. A recess 203 having a semi-circular radial cross-section is formed axially in the upper, flat face of the body to provide the channel into which a finger to be scanned is placed.

The radially outer face of body 201 is formed with a series of arcuate triangular cross-section ridges or grooves 204. The ridges have one arcuate face 205 substantially parallel to the entry face 202 formed at one end of body 201 so that the faces 205 may also serve as entry faces for the light from the array 200; the other arcuate faces 206 of the ridges facing in the opposite direction to the entry faces are also substantially parallel to one another and serve as the light exit faces from body 201. In the specific example where the body 201 is made from a material having a refractive index of 1.49, the angles of the various faces of the body 201 have the preferred values given in FIG. 7.

A rotary mechanism 210 similar to that shown in FIG. 3 causes a mirror 211 in the path of the light beam exiting body 201 through the arcuate exit faces 206 of body 201 to deflect the light onto a mirrored end face 212 of the shaft 213 on the mechanism is mounted. The array 200 is mounted on a transport carriage on which the rotary mechanism is carried so that it moves axially with the rotary mechanism, the axis of rotation of the mechanism 210 and the longitudinal axes of the body 201 and the array 200 all being substantially co-incident.

Light from the array 200 traverses the under-surface of the wall of channel 203 to illuminate the wall in a series of arcs. The light reflected from the under-surface of channel 203 is focused by a lens 214 carried on the rotary mechanism, reflected off mirror 211 and the mirrored end face 212 of shaft 213 onto a static sensor 215 located substantially upon the axis of rotation of shaft 213. In this case the rotating mechanism rotates about an axis which is substantially co-incident with the longitudinal axis of the optical body 201 and moves axially to and from substantially along that axis due to the nature of the optic paths achieved by the use of the triangular ridges on the surface of the optic body 201. Since in this case it is not necessary for there to be any vertical movement of the rotary mechanism 210, the drive system shown in FIG. 6 is modified so that the drive shaft 181 driving the carriage 180 is orientated substantially horizontally.

The device of the invention can be made simply and cheaply to provide a compact system for scanning the raised friction ridge pattern on a person's finger and producing an electrical signal output which can be processed in a pattern recognition system either to match the observed finger print against others held in a record or data bank or to compare the pattern with that held on an identity card or the like to verify that the person presenting the card is in fact the person to whom the card relates. The invention thus provides a means whereby data relating to a finger print can be readily collected in the form of an electronic record which can be transmitted electronically from the collection site to a remote data record for rapid identification and verification to take place, thus overcoming the need to hold substantial data records and image processing equipment at every location where identification is required.

We claim:

1. A device for scanning the surface of a generally cylindrical object carrying a raised pattern thereon so as to detect that pattern, which device comprises:
   a. a transparent optical body having a substantially arcuate configuration about a first axis and having a convergent radial cross-section, and a channel parallel to and substantially co-axial with that axis, which channel presents a surface substantially parallel to the said axis, upon which the object whose surface is to be observed can be placed, and the underside of which surface serves as the optical base face to the convergent radial cross-section to the optical body;
   b. a source of an incident light beam adapted to be directed onto a light entry face of the convergent cross-section of the optical body, the configuration of the optical body being such that the incident light beam is adapted to strike the under-side of the said optical base face at substantially the angle of total internal reflection for the material from which the optical body is fabricated and to be reflected through a light exit face of the convergent cross-section of the optical body;
   c. means for causing the said incident light beam progressively to traverse the said optical base face of the optical body; and
   d. a means for observing the light reflected from the underside of the said optical base face through a light exit face of the convergent cross-section of the optical body and for providing a signal dependent upon the intensity of the light detected.

2. A device as claimed in claim 1, wherein the radial cross-section of the convergent portion of the optical body has a generally triangular shape.

3. A device as claimed in claim 1, wherein the optical body comprises:
   a. a substantially central axial portion having a substantially circular or part circular radial cross-section, and a second portion extending radially outward of the central portion and having a generally triangular radial cross-section to provide a light entry face to the optical body and a light exit face from the optical body; and
   b. an axial substantially circular or part circular cross-section recess having its longitudinal axis substantially co-incident with that of the said central portion and adapted to receive the object to be scanned with at least part of the surface of the object in contact with the curved surface of the recess whereby light entering the optical body through said entry face is reflected at said curved surface and exits through said entry or exit face to be detected by the light observing means.

4. A device as claimed in claim 3, wherein the generally triangular radial cross-section of the convergent portion of the optical body is truncated.

5. A device as claimed in claim 1, wherein the optical body comprises:
   a. a substantially central axis portion having a substantially circular or part circular radial cross-section, the outer face of the central portion carrying an axial series of arcuate ribs or grooves having a generally triangular transverse cross-section to provide an axial series of light entry and exit faces; and
   b. an axial substantially circular or part circular cross-section recess having its longitudinal axis substantially co-incident with that of the central portion and adapted to receive the object to be scanned with at least part of the surface of the object in contact with the curved surface of the recess whereby light entering the optical body through said entry faces is reflected at said curved surface and exits through said exit faces to be detected by the light observing means.

6. A device as claimed in claim 1, wherein the said optical body extends over an arc of from 120° to 240°.

7. A device as claimed in claim 1, wherein the said optical body is configured so that light enters the optical body via said entry face at an angle ±5° to normal to the plane of the entry face, is reflected from said optical base face at ±10° to the angle of total internal reflection for the body in air and that the light reflected from said optical base face exits at ±5° to normal to the plane of the exit face.

8. A device as claimed in claim 1, wherein:
   a. the source of the incident light comprises a point light source adapted to direct a beam of light onto said optical base face for reflection onto a rotatable mechanism;
   b. there is provided a rotatable mechanism which is adapted to rotate about an axis substantially parallel to the longitudinal axis of said optical body, said rotatable mechanism carrying at least one first reflective surface adapted to receive said light beam reflected from said optical base face and to reflect it to a second reflective surface carried by said rotatable mechanism, which second reflective surface is adapted to reflect said light beam substantially along the axis of rotation of the rotatable mechanism;
   c. there is provided a sensor adapted to receive said reflected light from said second reflective surface; and
   d. means are provided for causing the said the rotatable mechanism to move axially with respect to the said optical body whereby the said mechanism is adapted to receive light from a plurality of positions both axially, and circumferentially upon said optical base face as said rotatable member rotates.

9. A device as claimed in claim 8, wherein said light source is adapted to direct its beam of light directly as the incident light beam onto the said optical base face of said optical body and is adapted to move axially with the said rotatable mechanism whereby the incident light beam progressively traverses said optical base face both axially and circumferentially as said rotatable member rotates.

10. A device as claimed in claim 8, wherein said source of light is an arcuate array of point light sources mounted with its longitudinal axis substantially co-incident with the longitudinal axis of the said optical body and adapted to direct a plurality of incident light beams onto the optical base face of said optical body; and the means for causing the rotatable mechanism to move axially with respect to said optical body also moves said array.

11. A device as claimed in claim 8, wherein:
   a. the source of the incident light beam is a stationary point light source which is adapted to direct an incident beam of light onto the rotatable mechanism;
   b. said rotatable mechanism carries at least one third reflective surface adapted to direct said incident light beam from said stationary source along a conical surface of revolution;
   c. means are provided for directing the light from said conical surface of revolution onto the said optical base face of the optical body;
whereby the said incident light beam is adapted to traverse said optical base face both axially and circumferentially as said rotatable member rotates.

12. A device as claimed in claim 8, wherein the rotatable mechanism is adapted to rotate about the longitudinal axis of a shaft, and at least one of said reflective surfaces is provided by a reflective inclined end face to said shaft.

13. The device of claim 1, wherein said optical body is sized to receive a finger of a person, said finger having an outer skin surface which is in contact with at least a portion of the surface of said channel when said finger is received within said channel.

14. A device for scanning the surface of a generally cylindrical object carrying a raised pattern thereon so as to detect that pattern, which device comprises:
   a. a transparent optical body having a substantially arcuate configuration about a first axis and having a convergent radial cross-section, and a channel parallel to and substantially co-axial with that axis, which channel presents a surface substantially parallel to the said axis, upon which the object whose surface is to be observed can be placed, and the underside of which channel surface serves as the optical base face to the convergent radial cross-section to the optical body;
   b. a source of incident light to be directed onto a light entry face of the convergent cross-section of the optical body, which source is an arcuate array of point light sources mounted with its longitudinal axis substantially co-incident with the longitudinal axis of the said optical body and adapted to direct a plurality of incident light beams onto the optical base face of said optical body, the configuration of the optical body being such that an incident light beam is adapted to strike the under-side of the said optical base face at substantially the angle of total internal reflection for the material from which the optical body is fabricated and to be reflected through a light exit face of the convergent cross-section of the optical body; and
   c. a means for observing the light reflected from the underside of the said optical base face through a light exit face of the convergent cross-section of the optical body and for providing a signal dependent upon the intensity of the light detected.

15. A transparent optical body suitable for use in scanning the surface of a generally cylindrical object carrying a raised pattern, the optical body comprising:
   a. a substantially central axial portion having a substantially circular or part circular radial cross-section;
   b. a second portion extending radially outward of the central portion and having a generally triangular radial cross-section to provide a light entry face to the optical body and a light exit face from the optical body; and
   c. an axial substantially circular or part circular cross-section recess having its longitudinal axis substantially co-incident with that of the said central portion, which recess presents an exposed surface substantially parallel to the said axis, the underside of which surface serves as the optical base face to the said second portion of the optical body, which recess is adapted to receive an object whose surface is to be scanned with at least part of the surface of the object in contact with the curved surface of the recess;
the configuration of the optical body being such that an incident light beam shone onto one exposed face of the said second portion of the optical body is adapted to strike the under-side of the said optical base face of the recess at substantially the angle of total internal reflection for the material from which the optical body is fabricated and to be reflected through the same or another exposed face of the said second portion of the optical body, whereby light reflected at said surface of the recess can be detected by a light observing means.

16. The transparent optical body of claim 15, wherein the generally triangular radial cross-section of the second portion is truncated.

* * * * *